United States Patent [19]

Umemura et al.

[11] 4,009,194

[45] Feb. 22, 1977

[54] CATALYTIC AMMOXIDATION OF OLEFINS TO NITRILES

[75] Inventors: Sumio Umemura; Kyoji Ohdan; Tokuo Matsuzaki; Yasuo Nakamura; Masao Sawazi, all of Ube, Japan

[73] Assignee: UBE Industries, Ltd., Ube, Japan

[22] Filed: Apr. 22, 1975

[21] Appl. No.: 570,499

[30] Foreign Application Priority Data

June 4, 1974 Japan .............................. 49-62512

[52] U.S. Cl. ............................ 260/465.3; 252/456; 252/469
[51] Int. Cl.$^2$ ...................................... C07C 120/14
[58] Field of Search ................................ 260/465.3

[56] References Cited

UNITED STATES PATENTS

| | | | |
|---|---|---|---|
| 3,642,930 | 2/1972 | Grasselli et al. | 260/465.3 X |
| 3,746,656 | 7/1973 | Shiraishi et al. | 260/465.3 X |
| 3,766,092 | 10/1973 | Honda et al. | 260/465.3 X |
| 3,872,148 | 3/1975 | Umemura et al. | 260/465.3 |
| 3,875,204 | 4/1975 | Ghirga et al. | 260/465.3 |
| 3,883,573 | 5/1975 | Milberger et al. | 260/465.3 |

*Primary Examiner*—Joseph Paul Brust

[57] ABSTRACT

Propylene or isobutylene is catalytically oxidized into the corresponding nitrile with improved conversions and yields. The catalyst consists essentially of the metals; (A) Mo, (B) Bi, (C) Co, (D) Fe and (E) Zr in the predetermined atomic ratios.

5 Claims, No Drawings

CATALYTIC AMMOXIDATION OF OLEFINS TO NITRILES

This invention relates to the synthesis of acrylonitrile or methacrylonitrile by catalytic ammoxidation of propylene or isobutylene. More particularly, it relates to a process for producing acrylonitrile or methacrylonitrile by contacting in the vapor phase a feed-mixture comprising propylene or isobutylene, ammonia and oxygen with a catalyst exhibiting an improved activity at a relatively low temperature.

Various catalysts have been heretofore proposed for use in the vapor phase catalytic ammoxidation of olefins to produce the corresponding unsaturated nitriles with a view to enhancing selectivity for a desired unsaturated nitrile without reducing conversion of the olefin feed. Known catalysts include combinations of two or more metals such as, for example, molybdenum, bismuth and optionally phosphorus as disclosed in Japanese Patent Publication 5870/61; tin and antimony as disclosed in Japanese Patent Publication 13966/62; uranium and antimony as disclosed in Japanese Patent Publication 24367/65; and iron and antimony as disclosed in Japanese Patent Publication 19111/63. Generally, however, it has been difficult to obtain both high selectivity to desired unsaturated nitrile and high conversion of olefin, i.e., there has been a need for controlling the conversion in order to obtain a high selectivity. With these known catalysts, the yield of unsaturated nitrile is at most approximately 70%. In general, since a long contact time and a high temperature, e.g. approximately 450° C or more are required, the yield of unsaturated nitrile per weight of catalyst is inevitably reduced, and the life of the catalyst is shortened.

The inventors have done extensive research on a catalyst for the ammoxidation of olefins, which comprises molybdenum, bismuth, iron and cobalt. However, it has been difficult with this catalyst to obtain 85% or more selectivity to nitriles, even when the conversion olefins is controlled, and to obtain more than 80% of yield.

Accordingly, a main object of the present invention is to provide an improved ammoxidation catalyst which gives better conversions and selectivities even at relatively low reaction temperatures, and exhibits a long catalyst life even when the reaction is conducted at relatively high temperatures.

Other objects and advantages of the present invention will become clear from the following description.

In accordance with the present invention, there is provided a process for producing acrylonitrile or methacrylontrile by catalytic ammoxidation of propylene of isobutylene, which comprises contacting a feed-gas mixture comprising propylene or isobutylene, ammonia and oxygen in the vapor phase at a temperature of 300 to 550° C for a period of 0.3 to 20 seconds with a catalyst consisting essentially of oxides of (A) molybdenum, (B) bismuth, (C) iron, (D) cobalt and (E) zirconium in the atomic ratios defined by the following formula $$Mo_a Bi Co_b Fe_c Zr_d O_e$$

wherein each of a, b, c, and d is a positive number indicating an atomic ratio of the respective metal to bismuth and falling within the following ranges, $a = 1.0$ to 20.0 preferably 5.0 to 15.0, $b = 1.0$ to 10.0, preferably 2.0 to 8.0, $c = 0.2$ to 5.0, preferably 0.5 to 4.0, and $d = 0.05$ to 4.0, preferably 0.1 to 2.0, and e is a positive number falling within the range of 6 to 86 and satisfying the average valency of the respective metals.

The catalyst of the present invention is advantageous over a metal oxide catalyst having a composition similar to that of the present invention but not containing zirconium in the selectivity to nitriles and the catalyst's mechanical strength.

The manner whereby the catalyst of the present invention is prepared is not critical. The catalyst may be prepared in any known manner provided that the respective metal components are present in the catalyst in amounts such that the catalyst satisifies the above formula. In general, the catalyst is prepared as follows. The respective metal-containing compounds are mixed with each other in an aqueous medium to form a precipitate, or mixed with a minor amount of water to form a slurry. The mixture, i.e., the precipitate or slurry, so formed in dried and then calcined usually at 400° C to 700° C.

The starting compounds may be oxides or salts, or a mixture thereof. As illustrations of the respective metal-containing compounds are, for molybdenum-containing compounds, ammonium molybdate, molybdenum oxide, ammonium oxychloromolybdate, molybdenum oxychloride and molybdenum chloride; for bismuth-containing compounds, bismuth nitrate, bismuth oxide, bismth hydroxide, bismuth hydroxynitrate and bismuth chloride; for iron containing compounds, iron oxide, iron nitrate, iron hydroxide and iron chloride; for cobalt containing compounds, cobalt nitrate, cobalt oxide, cobalt hydroxide, cobalt chloride and ammonium cobalt chloride; and for zirconium-containing compounds, zirconyl nitrate, zirconyl chloride, zirconium oxide and zirconium hydroxide.

One typical procedure for the manufacture of the oxide catalyst of the present invention will be illustrated. A predetermined amount of ammonium molybdate is dissolved in warm water. To this solution, a solution of a predetermined amount of bismuth nitrate in nitric acid and an aqueous solution of predetermined amounts of ferric nitrate, cobaltous nitrate and zirconyl nitrate are added by drops at the same time, while the aqueous slurry is stirred, thereby forming a slurry. The slurry is heated to dryness and calcined at 400° C to 700° C. The calcined product is pulverized and shaped into pellets or particles of desired shape and size. If a promotor element or carrier is used, it is added preferably at a stage prior to the drying of the precipitate.

It has proved by X-ray analysis that a predominant part of the catalyst of the invention is in the form of oxides each containing two or more metals such as, for example, cobalt molybdate, iron molybdate, zirconium molybdate, bismuth ferrate and bismuth zirconate, and a minor part of the catalyst is in the form of simple oxides each containing a single metal.

The catalyst may be used alone or in combination with any of the known carriers. As carriers, those which bring favorable effects for the reaction involved, such as silica, alumina, alumina-silica, silicate and the like which have been deactivated by, e.g. heat-treatment, may suitably be employed. These carriers may be used in any desired amounts.

The catalyst may be employed in either a fluidized bed or a fixed bed. The size and configuration of the catalyst grains are not critical but depend primarily on whether the catalyst is used in a fluidized bed or fixed bed. The catalyst may also be shaped or grained by suitable known methods in order to provide the required mechanical strength.

Propylene or isobutylene feed used in the process of the invention is not necessarily highly purified, but a mixture of propylene or isobutylene with saturated hydrocarbons such as propane and butane may also be used. However, any gas substantially influencing the ammoxidation reaction to any appreciable degree under the particular reaction conditions, for example, acetylene, n-butylene and the like, should preferable be excluded from the feed for the reaction since they may form undesirable by-products.

Likewise, other diluents which do not influence the ammoxidation reaction, may be present in the reaction mixture without deleterious effect. Such diluents include, for example, steam, nitrogen and carbon dioxide. The amount of diluent in the feed-gas mixture is preferably more than 0.5 moles per mole of propylene or isobutylene. Steam in the reaction mixture not only acts as a diluent but also exhibits effects to enhance the selectivity of the catalyst for the formation of acrylonitrile or methacrylonitrile and to make the activity of the catalyst durable. Accordingly, it is generally preferred to add steam to the feed-gas mixture when the reaction is conducted in a fixed bed. The amount of steam added is preferably at least 0.5 mole per mole of propylene or isobutylene. When the reaction is conducted in a fluidized bed, the water produced by the reaction has a similar effect and, accordingly, there is no need for the addition of steam.

As a source of oxygen which is used in the ammoxidation reaction of the invention, pure oxygen and any oxygen-containing gas may be used. Particularly, air may be advantageously used. The relative proportion of oxygen in the feed-gas mixture is suitably from 0.8 to 4 moles, and preferably from about 1.0 to about 2.5 moles per mole of propylene or isobutylene. Feeding of oxygen in excess of the above limit inevitably leads to formation of by-products such as carbon monoxide and carbon dioxide. On the contrary, feeding of oxygen less than the above range brings about a reduction of selectivity of the intended product.

A relative proportion of ammonia in the feed for the reaction mixture is suitably from 0.5 to 3 moles, and preferably from about 0.8 to 1.2 moles per mole of propylene or isobutylene.

The ammoxidation reaction is usually carried out under atmospheric pressure although slightly superatmospheric or slightly subatmospheric pressures may be used if desired.

The reaction is suitably carried out at a temperature ranging between 300° C and 550° C, preferably between 350° C and 500° C. Reaction temperatures exceeding the upper limit cause the decomposition of popylene or isobutylene, the reduction of selectivity and the promotion of side-reactions. For optimum results the reaction is carried out at approximately 400° C.

A contact time of 0.3 to 20 seconds, especially 0.5 to 15 seconds is preferred. A contact time exceeding the upper limit causes the decomposition of the reaction product and other undesirable side-reactions.

The invention is further illustrated by the following examples and comparative examples, which are for purposes of illustration only and should not be construed as limiting the invention in any sense. In these examples, "%" by weight unless otherwise specified, and "% conversion", "% selectivity" and "% yield" were calculated by the following equations.

$$\% \text{ conversion} = \frac{\text{moles propylene or isobutylene consumed}}{\text{moles propylene or isobutylene fed}} \times 100$$

$$\% \text{ selectivity} = \frac{\text{moles propylene or isobutylene converted to acrylonitrile or methacrylonitrile}}{\text{moles propylene or isobutylene consumed}} \times 100$$

$$\% \text{ yield} = \frac{\text{moles propylene or isobutylene converted to acrylonitrile or methacrylonitrile}}{\text{moles propylene or isobutylene fed}} \times 100$$

The yield used herein means a one pass yield.

EXAMPLE 1

318.6 g of ammonium molybdate [$(NH_4)_6Mo_7O_{24} \cdot 4H_2O$] was dissolved in 450 ml of water maintained at 80° C in a water bath, while being stirred. To this solution, were added dropwise at the same time, while being stirred a solution of 87.6 g bismuth nitrate [$Bi(NO_3)_3 \cdot 5H_2O$] in 110 ml of a 15% nitric acid and a solution of 72.9 g ferric nitrate [$Fe(NO_3)_3 \cdot 9H_2O$], 210.0 g cobaltous nitrate [$Co(NO_3)_2 \cdot 6H_2O$] and 9.6 g zirconyl nitrate [$ZrO(NO_3)_2 \cdot 2H_2O$] in 200 ml of warm water of 80°C. The slurry thus obtained was heated, while being stirred, to dryness to obtain a dry powder. The dry powder was shaped into tablets and then heated at a rate of 20° C/hr to 510° C and calcined at that temperature for 10 hours to prepare a catalyst.

The atomic ratio of metal components contained in the catalyst was Mo:Bi:CO:Fe:Zr: =10:1:4:1:0.2:37.4.

8 ml of the catalyst was packed into a U-shaped glass reaction tube having an inner diameter of 8 mm. A gaseous mixture of propylene, ammonia, air and steam, the molar ratio of the four components being 1.0:1.0:11.0:2.0, respectively, was passed through the catalyst-packet reaction tube maintained at 400° C at a flow rate of 150 ml/min. The contact time was 3.2 seconds.

The conversion of propylene, the selectivity to acrylonitrile and the yield of acrylonitrile were 94.2%, 85.2% and 80.3%, respectively.

EXAMPLE 2 through 10

Catalysts were prepared in a manner similar to that in Example 1 except that the proportion of the five metals was varied as shown in Table I, below. Using each of the catalysts thus prepared, the ammoxidation reaction of propylene was carried out in a manner similar to that in Example 1. Results are shown in Table I.

EXAMPLES 11 and 12

Using each of the catalysts similar to those used in Examples 4 and 8, ammoxidation of isobutylene was carried out following a procedure similar to that in Example 1 except that isobutylene was used instead of propylene. Results are shown in Table I, below.

Table 1

| Ex. No. | Atomic ratio of metal component in catalyst | | | | | | Reaction temperature (° C) | Conversion of propylene (%) | Selectivity to acrylonitrile (%) | Yield of acrylonitrile (%) |
| --- | --- | --- | --- | --- | --- | --- | --- | --- | --- | --- |
| | Mo | Bi | Co | Fe | Zr | O | | | | |
| 2 | 10 | 1 | 4 | 1 | 0.3 | 37.6 | 400 | 93.9 | 85.6 | 80.4 |
| 3 | 10 | 1 | 4 | 1 | 0.5 | 38.0 | 400 | 93.0 | 85.8 | 79.8 |
| 4 | 7 | 1 | 3 | 1.5 | 0.2 | 28.1 | 400 | 93.2 | 86.0 | 80.2 |
| 5 | 7 | 1 | 3 | 1.5 | 0.4 | 28.5 | 400 | 92.1 | 86.2 | 79.4 |
| 6 | 7 | 1 | 3 | 1 | 1.0 | 29.1 | 400 | 92.8 | 85.2 | 79.1 |
| 7 | 10 | 1 | 4 | 1 | 0.1 | 37.2 | 410 | 98.8 | 84.9 | 83.9 |
| 8 | 10 | 1 | 4 | 1 | 0.3 | 37.6 | 410 | 97.3 | 85.7 | 83.4 |
| 9 | 10 | 1 | 4 | 1 | 0.5 | 38.0 | 410 | 97.2 | 86.1 | 83.7 |
| 10 | 7 | 1 | 3 | 1.5 | 0.2 | 28.1 | 410 | 97.8 | 86.3 | 84.4 |
| 11 | 7 | 1 | 3 | 1.5 | 0.2 | 28.1 | 380 | 99.2*1 | 83.9*2 | 83.2*3 |
| 12 | 10 | 1 | 4 | 1 | 0.3 | 37.6 | 370 | 93.9*1 | 83.5*2 | 78.4*3 |

Note:
*1 Conversion of isobutylene
*2 Selectivity to methacrylonitrile
*3 Yield of methacrylonitrile

EXAMPLE 13

395.5 g of ammonium molybdate [$(NH_4)_6Mo_7O_{24} \cdot 4H_2O$] was dissolved in 644 ml of water while being stirred. To this solution, were added dropwise at 90° at the same time, while being stirred, a solution of 391.1 g cobaltous nitrate [$Co(NO_3)_2 \cdot 6H_2O$] and 90.5 g ferric nitrate [$Fe(NO_3)_3 \cdot 9H_2O$] in 428.5 ml of water and a solution of 108.7 g bismuth nitrate [$Bi(No_3)_3 \cdot 5H_2$] and 15.0 g of zirconyl nitrate [$ZrO(NO_3)_2 \cdot 2H_2O$] in 385 ml of a 10% nitric acid. Then 1667 g of silica sol ("Cataloid S-30" supplied by SHOKUBAI KASEI; $SiO_2$ content, 30%) was added to the slurry thus prepared The entire slurry was stirred for approximately one hour and then spray-dried at approximately 200° C. The dried product in the form of finely divided particles of 60 microns average diameter was heated to 600° C at a rate of 20° C per hour and calcined at this temperature for 10 hours.

The catalyst thus prepared contained metal components in the atomic ration of Mo:Bi:Co:Fe:Zr:O=10:1:6:1:0.25:39.5 and 50% of $SiO_2$.

150 ml (approximately 125 g) of the catalyst was packed into a fluidized bed reactor having an inner diameter of 36 mm and a length of 420 mm. A gaseous mixture of propylene, ammonia and air, the molar ratio of the three components being 1:1.1:12, respectively, was passed through the the catalyst-packed reactor maintained at 440° C at a flow rate of 1927 ml/min. The contact time was 4.68 seconds.

The conversion of propylene, the selectivity to acrylonitrile and the yield of acrylonitrile were 96.2%, 83.9% and 80.7%, respectively.

EXAMPLE 14

Following a procedure similar to that described in Example 13, a catalyst containing metal components in the atomic ratio of Mo:Bi:Co:Fe:Zr:O=10:1:5:1:0.5:40 and 50% of $SiO_2$ was prepared wherein the amounts of the starting compounds were varied with all other conditions remaining substantially the same. Using this catalyst, an ammoxidation reaction of propylene was carried out following a procedure similar to that described in Example 13.

The conversion of propylene, and selectivity to acrylonitrile and the yield of acrylonitrile were 97.6%, 84.5% and 82.5%, respectively.

COMPARATIVE EXAMPLE 1

A catalyst was prepared in a manner similar to that in Example 1 except that the zirconyl nitrate was not employed. The atomic ratio of metal components contained in the catalyst was Mo:Bi:Co:Fe:O=10:1:4:1:37. Using the catalyst thus prepared, ammoxidation of propylene was carried out in a manner similar to that in Example 1. The conversion of propylene, the selectivity to acrylonitrile and the yield of acrylonitrile were 94.5%, 82.1% and 77.6%, respectively.

COMPARATIVE EXAMPLE 2

A catalyst was prepared in a manner similar to that in Example 1 except that the proportion of the five metals was varied to Mo:Bi:Co:Fe:Zr:O=3:1:4:1:1:18. Using the catalyst thus prepared, ammoxidation of propylene was carried out in a manner similar to that in Example 1. The conversion of propylene, the selectivity to acrylonitrile and the yield of acrylonitrile were 91.3%, 73.8% and 67.4%, respectively.

COMPARATIVE EXAMPLE 3

Following a procedure similar to that described in Example 13, a catalyst containing metal components in an atomic ratio similar to that in Example 13 except that no zirconium was contained therein, was prepared and tested for its catalyst activity.

The conversion of propylene, the selectivity to acrylonitrile and the yield of acrylonitrile were 92.5%, 76.0% and 70.3%, respectively.

What we claim is:

1. A process for producing acrylonitrile or methacrylonitrile by catalytic ammoxidation of propylene or isobutylene, which comprises contacting a feed-gas mixture comprising propylene or isolutylene, ammonia and oxygen in the vapor phase at a temperature of 300° C to 550° C for a period of 0.3 to 20 seconds with a catalyst consisting essentially of as the sole catalyst a predominant amount of oxides each containing two or more metals and a minor amount of simple oxides each containing a single metal, said catalyst having the composition defined by the following formula $Mo_aBiCo_b$-$Fe_cZr_dO_e$ wherein each of a, b, c, and d is a positive number indicating an atomic ratio of the respective metal to bismuth and falling within the following ranges, $a = 5.0$ to $15.0$, $b = 2.0$ to $8.0$, $c = 0.5$ to $4.0$ and $d = 0.1$ to $2.0$, and e is a positive number falling within the range of 6 to 86 and satisfying the average valency of the respective metals; and said catalyst being the calcined residue of a mixture formed by mixing in an aqueous system the respective metal-containing compounds, said respective metal-containing compounds being in the form of oxide, salt or a mixture thereof.

2. A process according to claim 1 wherein said feed-gas mixture comprises propylene or isobutylene, ammonia and oxygen at proportions such that the molar ratio of ammonia to propylene or isobutylene is within the range of 0.5:1 to 3:1 and the molar ratio of oxygen to propylene or isobutylene is within the range of 0.8:1 to 4:1.

3. A process according to claim 1 wherein said feed-gas mixture further comprises at least 0.5 moles of steam per mole of propylene or isobutylene.

4. A process according to claim 1 wherein the reaction temperature is within the range of 350° C to 500° C.

5. A process according to claim 1 wherein the contact time is within the range of 0.5 to 15 seconds.

* * * * *